(12) United States Patent
Riff et al.

(10) Patent No.: US 7,685,005 B2
(45) Date of Patent: Mar. 23, 2010

(54) MEDICAL DEVICE SYSTEMS IMPLEMENTED NETWORK SCHEME FOR REMOTE PATIENT MANAGEMENT

(75) Inventors: Kenneth M. Riff, Orono, MN (US); Gregory J. Linden, Shorewood, MN (US); Kurt R. Smith, Boulder, CO (US)

(73) Assignee: Medtronic, Inc., Minneapolis, MN (US)

( * ) Notice: Subject to any disclaimer, the term of this patent is extended or adjusted under 35 U.S.C. 154(b) by 1074 days.

(21) Appl. No.: 09/943,193

(22) Filed: Aug. 29, 2001

(65) Prior Publication Data

US 2002/0082480 A1 Jun. 27, 2002

Related U.S. Application Data

(60) Provisional application No. 60/228,961, filed on Aug. 29, 2000, provisional application No. 60/228,674, filed on Aug. 29, 2000, provisional application No. 60/228,686, filed on Aug. 29, 2000, provisional application No. 60/228,685, filed on Aug. 29, 2000, provisional application No. 60/228,645, filed on Aug. 29, 2000, provisional application No. 60/228,699, filed on Aug. 29, 2000, provisional application No. 60/228,698, filed on Aug. 29, 2000, provisional application No. 60/228,697, filed on Aug. 29, 2000, provisional application No. 60/228,696, filed on Aug. 29, 2000.

(51) Int. Cl.
*A61B 5/00* (2006.01)
*G06F 19/00* (2006.01)

(52) U.S. Cl. .................. 705/3; 705/2; 705/4; 600/300; 707/100

(58) Field of Classification Search .................. 600/300, 600/528; 128/904; 707/100; 705/2–3
See application file for complete search history.

(56) References Cited

U.S. PATENT DOCUMENTS 5,508,912 A 4/1996 Schneiderman ................ 705/3

(Continued)

FOREIGN PATENT DOCUMENTS

EP 1 022 035 A1 7/2000

(Continued)

OTHER PUBLICATIONS

Lu et al., "A Conceptual Model of Data Warehousing for Medical Device Manufcturing," IEEE, Proceedings of the 22$^{nd}$ Annual EMBS International Conference, Jul. 23-28, 2000, Chicago, IL, p. 1279-84.

(Continued)

*Primary Examiner*—Gerald J. O'Connor
*Assistant Examiner*—Michelle Linh Le

(57) ABSTRACT

A system and method for computer enabled network patient management of medical devices used in chronic disease management. Utilizing web site and push alert notification of alert level physiologic data derived via analysis of continuous stream wireless data transmissions from a patient, a full cycle improvement over existing modalities is achieved. Proxy and medical device user integration and access is enabled to achieve further contribution to the technical advantages of the system.

19 Claims, 8 Drawing Sheets

U.S. PATENT DOCUMENTS

| | | | | |
|---|---|---|---|---|
| 5,544,661 | A | * | 8/1996 | Davis et al. .................. 600/513 |
| 5,619,991 | A | | 4/1997 | Sloane ........................ 600/300 |
| 5,633,910 | A | | 5/1997 | Cohen .......................... 379/38 |
| 5,752,976 | A | | 5/1998 | Duffin et al. .................. 607/32 |
| 5,781,442 | A | | 7/1998 | Engleson et al. ............. 700/214 |
| 5,819,092 | A | | 10/1998 | Ferguson et al. ............. 717/113 |
| 5,899,998 | A | | 5/1999 | McGauley et al. |
| 5,911,687 | A | * | 6/1999 | Sato et al. .................... 600/300 |
| 5,915,240 | A | | 6/1999 | Karpf |
| 5,924,074 | A | | 7/1999 | Evans |
| 5,987,519 | A | | 11/1999 | Peifer et al. .................. 709/230 |
| 5,991,476 | A | * | 11/1999 | Baney et al. ................... 385/16 |
| 5,997,476 | A | * | 12/1999 | Brown .......................... 600/300 |
| 6,004,276 | A | | 12/1999 | Wright et al. ................ 600/508 |
| 6,006,191 | A | * | 12/1999 | DiRienzo ........................ 705/2 |
| 6,022,315 | A | | 2/2000 | Iliff |
| 6,050,940 | A | | 4/2000 | Braun et al. ................. 600/300 |
| 6,101,478 | A | * | 8/2000 | Brown ............................ 705/2 |
| 6,108,635 | A | | 8/2000 | Herren et al. ................... 705/2 |
| 6,112,194 | A | | 8/2000 | Bigus ........................... 706/11 |
| 6,168,563 | B1 | * | 1/2001 | Brown .......................... 600/301 |
| 6,171,237 | B1 | | 1/2001 | Avitall et al. ................. 600/300 |
| 6,192,114 | B1 | | 2/2001 | Council .................. 379/114.14 |
| 6,203,495 | B1 | | 3/2001 | Bardy ........................ 600/301 |
| 6,205,437 | B1 | | 3/2001 | Gifford ........................ 705/75 |
| 6,206,829 | B1 | | 3/2001 | Iliff ............................ 600/300 |
| 6,221,011 | B1 | | 4/2001 | Bardy ........................ 600/300 |
| 6,249,705 | B1 | * | 6/2001 | Snell ............................ 607/59 |
| 6,250,309 | B1 | * | 6/2001 | Krichen et al. ............... 128/899 |
| 6,253,193 | B1 | | 6/2001 | Ginter et al. ................... 705/57 |
| 6,260,050 | B1 | | 7/2001 | Yost et al. ................. 707/501.1 |
| 6,261,230 | B1 | | 7/2001 | Bardy ........................ 600/300 |
| 6,264,614 | B1 | * | 7/2001 | Albert et al. ................. 600/528 |
| 6,364,834 | B1 | * | 4/2002 | Reuss et al. ................. 600/300 |
| 6,416,471 | B1 | * | 7/2002 | Kumar et al. ................ 600/300 |
| 6,602,469 | B1 | * | 8/2003 | Maus et al. .................. 422/68.1 |
| 6,669,631 | B2 | * | 12/2003 | Norris et al. ................. 600/300 |
| 6,834,341 | B1 | * | 12/2004 | Bahl et al. ..................... 713/156 |
| 6,934,372 | B1 | * | 8/2005 | Lynam et al. ................ 379/111 |
| 2001/0044586 | A1 | * | 11/2001 | Ferek-Petric ................ 600/523 |
| 2002/0059587 | A1 | * | 5/2002 | Cofano et al. ................. 725/35 |
| 2002/0169636 | A1 | * | 11/2002 | Eggers et al. ................... 705/3 |

FOREIGN PATENT DOCUMENTS

| | | |
|---|---|---|
| WO | WO 98/15910 | 4/1998 |
| WO | WO 98/24358 | 6/1998 |
| WO | WO 00/10455 | 3/2000 |
| WO | WO 00/29983 | 5/2000 |
| WO | WO 01/22265 | 3/2001 |
| WO | WO 02/17593 A2 | 2/2002 |

OTHER PUBLICATIONS

Quintana, Y., "User Modelling and Information Filtering for Consumer Health Information," *IEEE*, 0-7803-4053-1, p. 4207-10 (1997).

* cited by examiner

MEDICAL DEVICE SYSTEMS IMPLEMENTED NETWORK SCHEME FOR REMOTE PATIENT MANAGEMENT

RELATED APPLICATIONS

This application claims priority from U.S. Provisional Application Ser. Nos. 60/228,961, 60/228,674, 60/228,686, 60/228,685, 60/228,645, 60/228,699, 60/228,698, 60/228,697 and 60/228,696, all filed on Aug. 29, 2000, and also from U.S. Ser. No. 09/935,019, entitled "Medical Device Systems Implemented Network System For Remote Patient Management," filed Aug. 22, 2001.

FIELD OF THE INVENTION

The invention relates to medical devices implemented and communicable through network systems such as the internet. More specifically, the invention relates to patients wearing implantable or externally mounted medical devices in which the devices are communicable to remote healthcare professionals or expert centers for a variety of purposes.

BACKGROUND OF THE INVENTION

Medical devices such as cardiac systems, drug delivery systems, neurological products and similar other products are implanted in patients for various clinical reasons. Some of these devices may collect and document data on a continuous basis. However, the state of the art is currently to ask patients to see their doctors or other health professionals on a regular basis to retrieve and check the physiological data collected in these devices.

As medical devices become very sophisticated, in both reliability and maintainability, the need for patients to visit their doctors on a regular basis may not be required by coverage plans or for other rationale. Various attempts to remotely engage or monitor patients or medical devices/systems have been suggested, such as for example those generally described in U.S. Pat. Nos. 6,261,230; 6,206,829; 6,221,011 B1; 6,203,495 B1; 6,250,309 B1; 6,168,563 B1; 6,108,635; 6,101,478; 6,050,940; 6,004,276; 5,987,519; 5,911,687; 5,781,442; 5,752,976; 5,633,910; 5,619,991; 5,544,661; and 5,508,912. However, for patients with chronic disease, the management of the disease has become a critical aspect which affects both the cost of health care and the quality of life of the patient. Accordingly, patients with implantable medical devices or externally mounted devices that monitor critical medical data are either kept in hospitals or the patients are required to visit their physicians on a very regular basis.

Accordingly, a data transfer and review system that enables doctors and physicians to monitor patients on an as-needed basis and as frequently as possible, while allowing patients to stay at home, is a highly desirable service. Such a service would also enable the patient to have access to their own personal data by enabling real time data management and review by professionals as well as the patient. Further, medical devices could be designed to enable patients to be interactive with the devices that are monitoring their physical and medical parameters such that the patient could also be involved in managing their disease on a day-to-day basis. More specifically, if patients are allowed to have access both to the operation of their device and reports that are stored in them, they may have sessions with their doctors and will also be well-informed in managing their disease, thereby becoming active partners in the management of their own disease. Various economic opportunities may also arise from such accomplishments.

Various online systems or data mining systems are also known and described generally in U.S. Pat. Nos. 6,260,050; 6,253,193; 6,205,437; 6,192,114; 6,112,194; 5,819,092; and International Publication WO 01/22265.

SUMMARY OF THE INVENTION

An internet- or equivalent-based system and method for a service is disclosed which connects a remote patient to a database network for medical device data exchange and review. The system and method includes providing a web-site having a user interface wherein the user interface includes a secure sign-in input to access a medical device database network site, receiving at the web-site inputs associated with a specific medical device and patient, confirming the identity of the medical device and the patient, and enabling the patient to access the database to use the service. A further aspect of this system and method of doing business is to connect remote users to a database network for medical device data exchange and review by identifying authorized users to access the database network and generating advantages, including revenue streams of a type and quality not previously possible.

DESCRIPTION OF THE INVENTION

Figure 1:
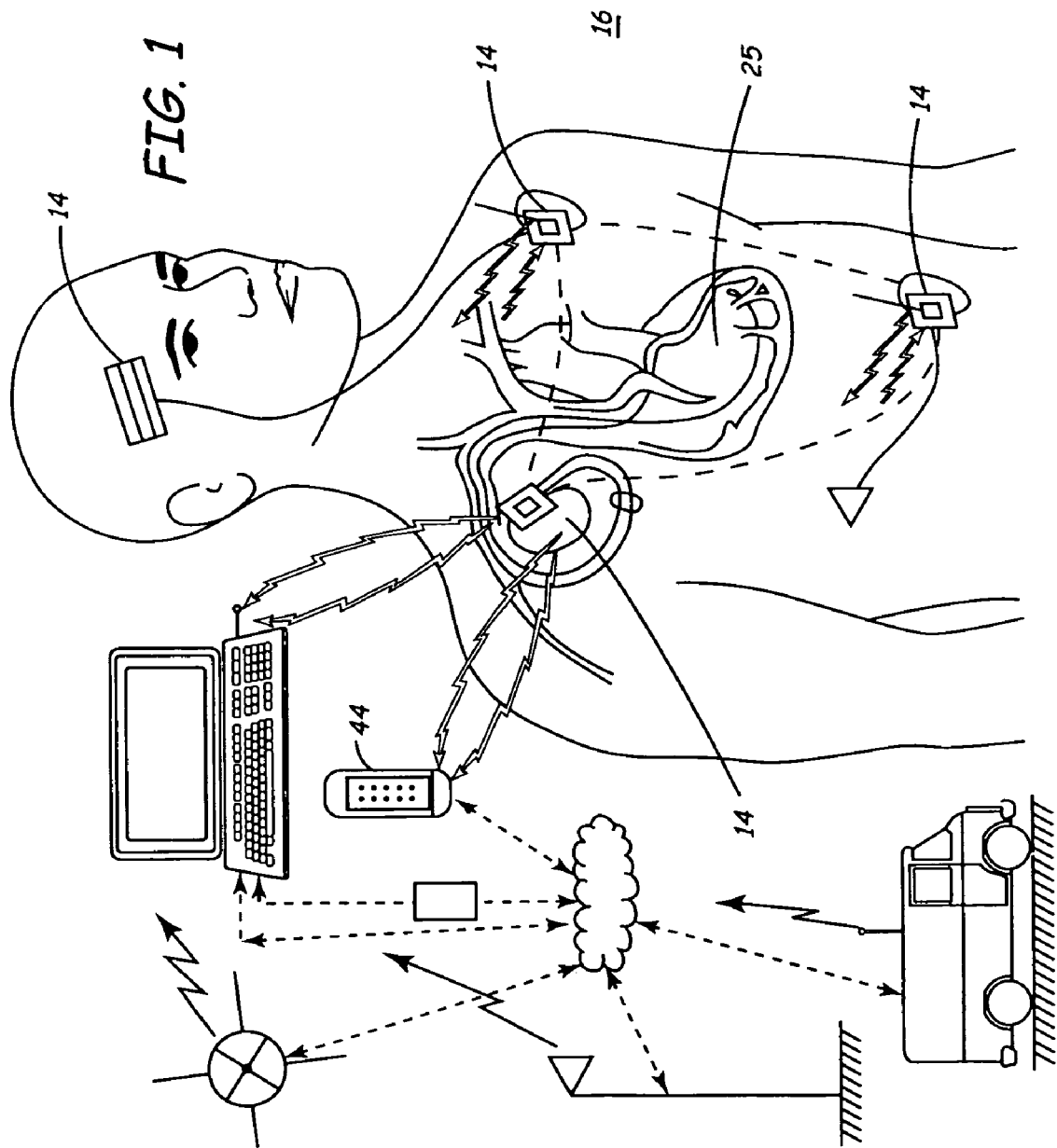
FIG. 1 is a schematic representation of a patient with exemplar implanted medical device components interfacing with a remote patient management network.

Attempts to provide improved healthcare to patient populations using technological methods have met with varying degrees of success. Indeed, however, a very critical problem has emerged in most such efforts. The patients and healthcare providers alike risk increased isolation as the use of technology increases. This isolation and sense of de-personalization in the healthcare system is often a chief complaint of patients, as well as a source of potential conflict which could actually impede the formation of candid dialogue which is at the core of the best models of patient-physician interface.

Another problem exists in that no actual system for fall-cycle healthcare enablement exists without substantial human intervention for data handling. Although various patents suggest systems and methods for either direct healthcare system improvement or revenue generating systems and methods which might be useful in healthcare providing (such as those noted above), these are essentially inoperative or impractical schemes.

Assignee of the Applicants (Medtronic, Inc.) has developed medical devices that are able to detect large amounts of valuable patient specific information and process that information so as to decide whether one or more specific actions is appropriate, including for example whether applications of therapy or ongoing diagnosis is merited. This is technology that has emerged in application of implantable medical devices over the last several decades, and has transformed many lives due to its use by Medtronic and other companies. However, Applicants have now identified new and improved mechanisms by which the technical means of harnessing the ongoing and simultaneous revolutions in medical device technologies and information technologies to achieve a new level of patient and healthcare provider satisfaction, quality of care, improved service, improved efficiencies and improved economics is realized. This combination of new technical processes has overcome the combined technical problems associated with: sensing highly specific signals, parsing and validating high volumes of data, power management of implanted medical devices, bandwidth allocation to integrate all levels of a web-enabled network among multiple foreign users, timing and structures of signals and processing, accessibility and security, display limitations and demands, data routing in multiple paths including wireless paths, partial user unfamiliarity with technology, partial user incapacity, automatic assessment and further handling of individual device user data, non-integrated clinical guidelines, and other challenges. The technical effect of the selected protocols along with the application of advanced information technology has resulted in a significant technical contribution to the art of integrated network-based signal and resource management for programmable and high relevance detected data signals.

Applicants have recognized that a remarkable innovation is achieved in deeply utilizing the now very robust data collection capabilities of various medical devices and integrating that (explicit and/or implicit) information (either before, during or after analyzing or processing the information) into a data network. This causes integration of the patient and healthcare providers, or others, into a collaborative effort resulting in patient-specific healthcare improvement and very dynamic system efficiencies. This is a pioneering effort in identifying a combination of historic problems, applying technical methodology to combine the best medical and information technologies resulting in a solution which transforms the way resources are allocated, which in turn leads to improvements for care of patients with various diseases and conditions, particularly those having chronic conditions.

At one level, the contributions of this invention enable economic functionality to attach to highly innovative technical solutions. These technical solutions to patient care and chronic monitoring yield data in seeming orders of magnitude greater in quality and quantity than in just the recent past. For example, Applicants' devices automatically sense, retrieve, transmit, process, and store greater than $10^{10}$ heart beats (i.e. cardiac rhythm elements) in a time of just a small number of hours, continuously over an extensive patient population. When this data is combined with data obtained and automatically processed during cardiac procedures in operating or emergency rooms, then the volume of this rich database is further enlarged. When this data is analyzed, automatically, with software-based algorithms and other tools, then the data is transformable to various knowledge-enhanced value-added formats. Such formats may be of various types. For example, signal structuring and data formatting (either prior to and/or as a consequence of initial processing of transmitted physiological data) may enable different users of the different formats to have resultant data-based tools available for use in numerous different applications or tasks. Examples include different uses and/or formats of mined physiologic data to be used with great advantage and economic value by: physicians, health care systems, information networks (from which various laboratories access high relevance information), Disease Management Organizations (which enables very high quality patient interactions use of point of care, instruments, and timely clinical guidelines), internet users, (internet companies, health sites, patient advocacy groups, clinical trial organizations, pharmaceutical companies and individual patient web sites), retailers, and medical product or device companies (for research and development, product planning, post-market surveillance, sales and marketing, and clinical database work). These users require many different tools, forms of data, for individual and often interactive production of their services and other products. Accordingly, a provider of high relevance data-based products, either raw or rendered, creates substantial value within numerous systems, each of which is subject to its own economic rules and metrics. Regardless of any differences or similarities among these data users, they each receive a value-added product for their constituencies when the information flow or mere availability of this data is enabled.

In addition to the data and the data flow, there are various new uses for this physiologic data which occur as a result of the underlying inventions disclosed herein, and which will be discussed further below. Generally, these innovations create knowledge enhanced value, integration enhanced value, and timing enhanced value. These value enhancements in turn enable previously unknown services and products to be provided to various consumers, such as knowledge repositories; data mining tools; academic research tools; surgical techniques; tools, and planning; device and service-assisted outcomes monitoring and improvement; and mapping or visualization tools. When previously inaccessible or non-useable data of high relevance is rendered available and in appropriate structure or format, then the above advantages are made possible. As such, the technical advantages and contributions of Applicants is realized.

In one example, patients having advanced cardiovascular disease (and their care givers) may utilize one aspect of this invention to great advantage. Using one or more medical devices 14, such as the implantable cardiac-related devices known as either the Medtronic Chronicle device or the GEM III DR device, shown in patient 20 of FIG. 1, a patient's cardiac system is closely monitored. This figure also illustrates alternate examples of device 14 which includes neurologic device 14 and drug infusion device 14 as well. The invention may utilize a device such as those noted above which is implanted for sensing directly in a cardiac chamber 25, and which may have more data acquisition capability and processing power than any other known implantable on earth, or even a more limited capability device. Such a powerful data acquisition platform is able to store a wealth of information regarding cardiac and overall patient physiologic data in the onboard RAM of the device that can be uploaded through wireless technology, such as radio frequency (RF) telemetry, telemetry B or C, or the like. Following acquisition of this medical data from inside the body, then advanced information and communication technologies are utilized to format and communicate this information to other locations or users in a manner which eliminates or virtually obviates human intervention for various levels of processing of the physiologic data.

In one embodiment, another device, shown in representative manner as device 44 in FIG. 1, is arranged to be near the patient and to obtain the information from the implanted device and transmit the data to a remote network. Device 44 may be alternately described as a remote interrogator or by other terminology, which is not meant to limit its actual technical characteristics in any way, but rather to identify a data communication device for use with medical devices as generally described herein.

As shown in FIGS. 1-7, a secure transmission of the physiologic data from the patient then occurs, with the data flowing to a robust network where it can be stored, processed, analyzed and presented for viewing via a web browser or other interfaces. These technologies have been combined and improved with the specific purpose of providing a reliable, scalable, secure and accessible system for worldwide real-time use of the patient's data. This is an extraordinary, full cycle, breakthrough over known limited systems for disease and patient management. Indeed, this invention re-organizes and prioritizes patient care in a manner not previously known along a new model of data and human interaction. In the cardiac example above, information about the patient's heart is online and accessible at all times. The system provides the physician and others with a continuous, longitudinal record of cardiac status rather than the snapshot, or limited view, that is received when the patient comes into a clinic. This is also real-time and continuous, rather than reactively responsive and subject to any specific event or to known monitoring device availability or limitations. Physicians and other users may then utilize this new system and methods to implement timely, systematic therapeutic regimens for their patients—as well as for other purposes. It is recognized that either the virtual or the physical locations of certain elements of this system, and methods of performing the services and advantageous steps of the invention, may be optionally determined to occur in either one or more jurisdictions depending on the element, step, signal, perspective or advantage enabled. In addition, appropriate data use and other security authorizations or measures are fully contemplated, and may be relevant to judging the utilization and scope of challenges successfully overcome by this invention.

Using this invention, the patient, and optionally the patient's friends, family, and others, become active participants in the management and/or progression of the patient's health. This enables the patient to be empowered as a collaborator through the system's patient portal, where he or she can access individualized educational, monitoring and self-care programs at any time from virtually any location. Although a deep and rich variety of data is acquirable, data having the most relevance for the specific patient may be designated for sensing, e.g. a patient's monitored signals may include intracardiac pressures, heart rate, physical activity, or other signals having the most utility for the patient. This process of continuous data collection is then supplemented by the uploads of all or some of the data to an external proximate device (i.e. in home, office or car) for transmission of the critical physiologic data securely to a healthcare management network. Physicians or others can access the network via a Web site at any time and review screens that present summary information from the latest upload, trend information accumulated over time, and/or detailed records from specified times or problem episodes.

The invention has the potential to dramatically transform the management of chronic diseases like heart failure and cardiac arrhythmias, neurologic conditions, or conditions requiring drug infusions, and other health needs relating to particularly long-term health conditions. It will improve the quality of care by providing the physicians with real-time data about their patients' physiological (and maybe other) conditions so that corrective actions may be taken in a timely manner, if appropriate. This invention will improve the quality of life for the patients, enabling them to remain in their homes or travel as desired without the same level of constant worry concerning an emergency hospitalization. The invention will result in dramatic lowering of the cost of managing chronic disease by reducing unnecessary hospitalizations and clinic visits. Perhaps more importantly, this system and methodology will help restore the close bond of the patient-physician relationship through the power of direct connectedness and the proliferation of high relevance understandable knowledge to all participants in the process. For example, the system and methodology makes personalized health information, even detailed information on the performance of a patient's own heart, available to the patient and loved ones (or other advocates of the patient) through an interactive web or mobile portal. Other users of patients' data are now fully enabled to utilize this data for individual patient and systemic healthcare improvements, as authorized. Analyses of this system have already observed many of these very positive effects, synergies and impacts.

In addition to the profound implications for quality of care, standard of care, and related issues in relation to this invention, the financial and business impact of this system and methodology is quite revolutionary. The system is designed to more successfully manage people with chronic diseases by leveraging the Internet or similar communication medium that allows continuous or near continuous real-time data access. The interaction with clinical researchers of users of this invention is also valuable. This degree of interaction allows for more rapid and in-depth clinical analysis of disease symptoms and treatments, thereby reducing the overall costs of such efforts. Such real- time access to patient data also facilitates administration of drug and other therapy in a more responsive and economical fashion. The involvement of the patient and the patient's advocate(s) promotes improved communication and outcomes. Combining this with the known patient desire for greater convenience and a closer connection to the physician, then the advantages of this invention are many.

Figure 2:
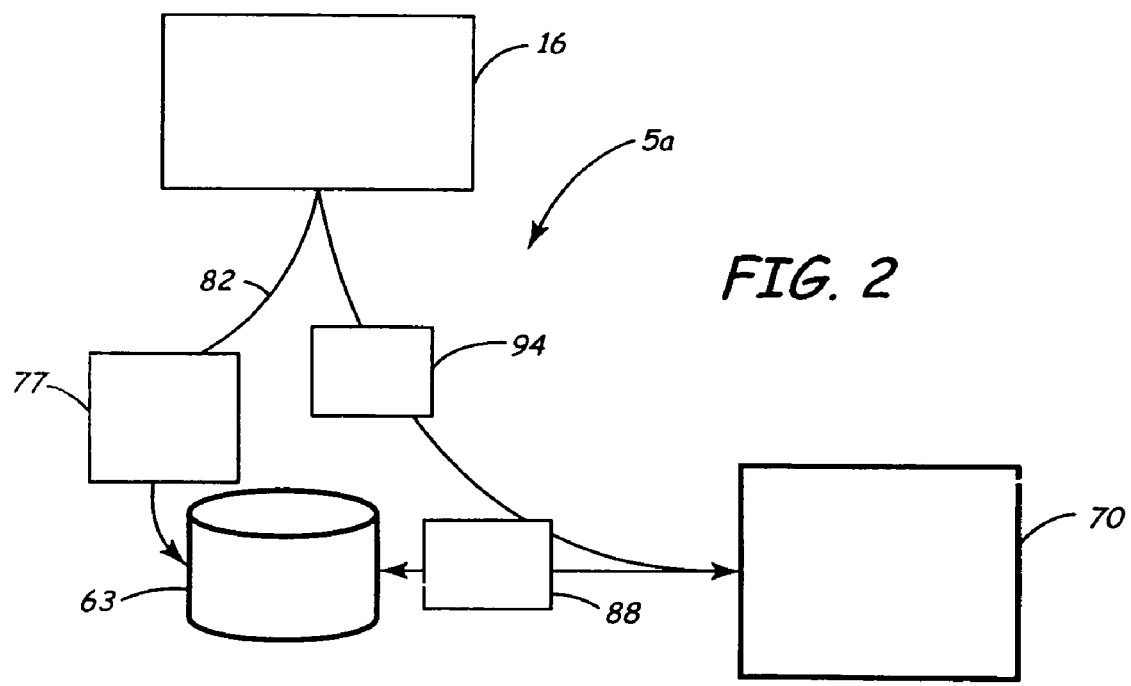
FIG. 2 is a schematic diagram of the system and data flow of the invention.

FIG. 2 is a schematic representation of a portion of system 50 designed for interacting and managing care for a patient 16 having at least one interactive medical device, such as for example an implanted cardiac, neurologic, infusion or other device. It is recognized that partially implanted or external devices may also be incorporated into the full scope of this disclosure, provided such devices or components are capable of operating in the robust data environment of this invention. FIG. 2 illustrates the relation between patient 16, an electronically accessible patient management database 63, and a web-based site 70. Patient management database 63 is configured for receipt, storage, processing, and other transmission and handling of information related to the healthcare status of patients administered by system 50, including patient 16. Physiologic data 77 is uploaded via wireless 82 or other transmission means from devices in or in communication with devices in or on patient 16, and is of a content and format designed to selectively provide essential high relevance information regarding all manner of monitored disease etiology and system functionality. This information is automatically uploaded via path 82 to the database 63, possibly in response to interrogation routines, and subject to power management, disease stage, and other considerations. Data 77 is then registered or otherwise processed as appropriate and transmitted in various form to at least one web-based site 70, configured to allow access by the patient and others, as will be further discussed below, and as depicted in path 94 with one or more secure sign-in protocols included. It is recognized that patient medical device data 88 may also flow from web-based site 70 back to patient management database 63.

Figure 3:
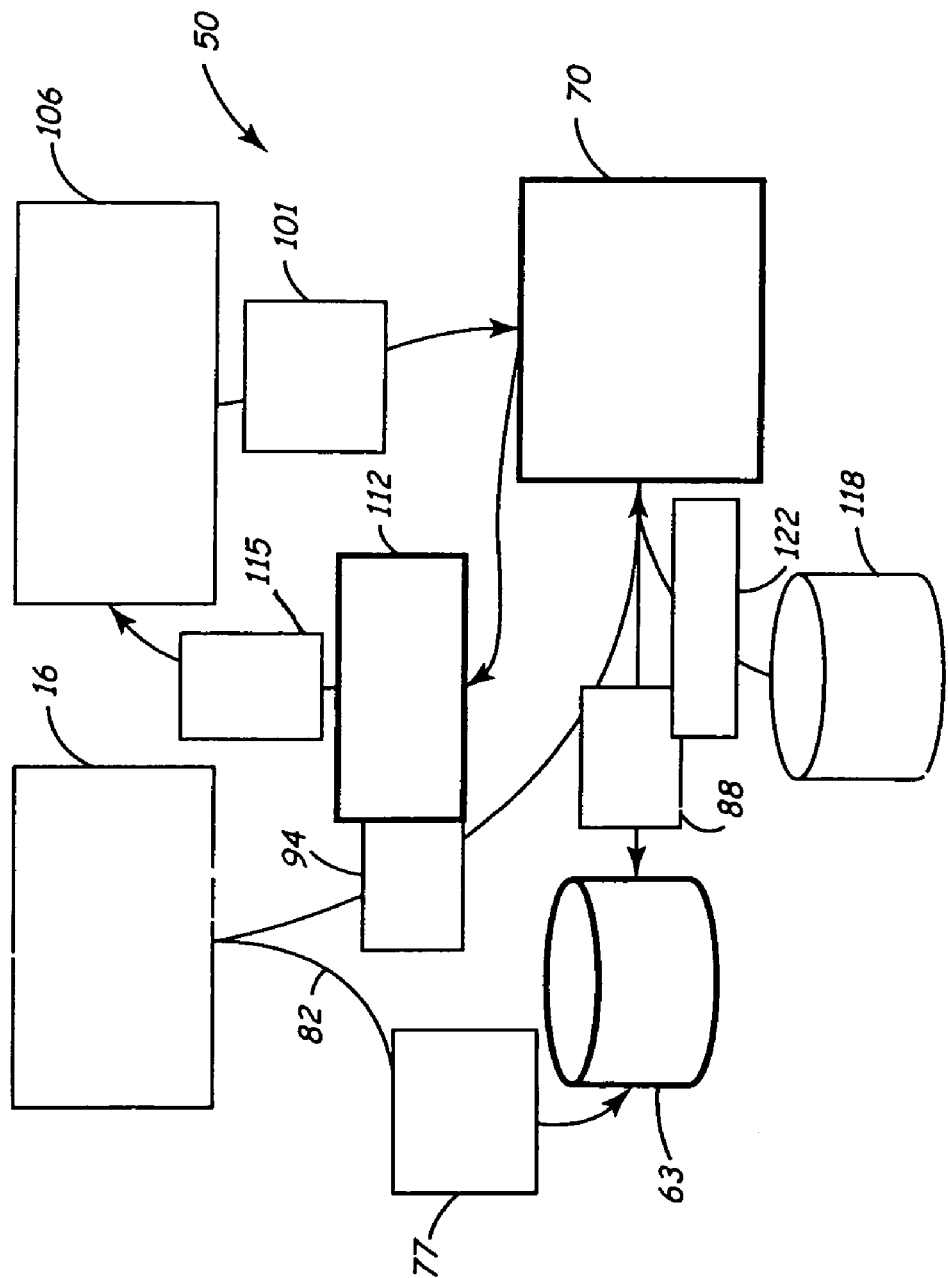
FIG. 3 is a schematic diagram of the system and data flow of the invention.

FIG. 3 depicts web-based or equivalent site 70 as a platform which is accessible via secure sign-in 101 by a first medical provider 106 such as a nurse or other type of provider responsible for the care and first stage monitoring of patient 16. A variety of interactions are enabled by this relationship, including use of web-based site 70 as a destination for secure access to provide and receive information pertinent to the care of patient 16, including unique and high relevance physiologic data 77 detected from within one or more patients and transmitted via patient management database 63. In the event of physiologic data 77 containing information meeting certain criteria, such as activating triggers or set points based upon certain analytics, differentials or algorithmic metrics, then the patient management database 63 and the web-based site 70 may be configured to provide an automatic event notification service signal 112 to a display or other data receiving device of one or more medical providers, such a first medical provider 106. In one example, automatic event notification service signal 112 may be pushed via an SMTP.net message, shown for example as signal format 115, to medical provider 106 computer or other display. These displays, and others contemplated herein, may also include an automatic pushed signal via electronic mail, pager, cellular phone, WAP cellular phone, telephone call, facsimile, mobile wireless device, stylus tablet, or others. This automatic event notification service signal 112 may be used to alert provider 106 of a health related signal anomaly or other indication which may require prompt action to assist the patient, and is likely not necessarily a secure message but rather a rapid message, which may be more preferable. Accordingly, in one embodiment, the rapid automatic event notification service signal 112 includes a link accessible by the medical provider to rapidly access the data of interest from the web-site 70, and which requires a response by the recipient. Such signal 112, and others herein, may also activate an automatic time notated archival feature for later reference for various purposes. As in much of this invention, this path may require a security validation or authentication, depending on system, patient service, and legal requirements. Various biometric or other cipher-like technologies may be utilized, although a smart card or other intelligent and convenient tool may be preferred. For example, one embodiment of a smart card may be able to record medical updates of the patient's health record whenever it is used for access authentication, and thus provide an element of redundancy to the medical record.

First medical provider 106, or others described herein, may be granted secure single sign in rights to facilitate rapid access for the designated individual to the various elements of this system and architecture. This feature may also be transportable as that professional traverses among electronic links in order to ensure connectivity during the response to a detected event, or the access may be a graded access according to an event severity algorithm or other grading technique.

A further feature may include a link or other access to a database 118 or other medium having an electronic medical health record 122 of the patient who is the source of the automatic event notification service signal 112. In this manner the patient's pertinent medical history may be presented along with the new data which caused the medical alert, thereby allowing the medical provider to have proper perspective and accuracy as to the specific patient. In one embodiment, electronic medical health record 122 is a data rich format such as that known as Extended Markup Language (XML), although various data formats may be utilized to provide the advantages and data contemplated. Moreover, in one embodiment, a single page format is preferred but not required, in order to allow the efficiencies of a template that may be efficiently structured for a single screen display of the most critical information to a final decision maker. This may include a summary, a waveform, a differential diagnosis analysis, coding options, trending graphs, overlays of patient history versus current data, or other high relevance formatted data appropriate to that patient or patient class. Rapid augmenting/updating of that formatted information is also possible, when desired, due to the configuration of this system and the rich data mining capabilities it enables.

Figure 4:
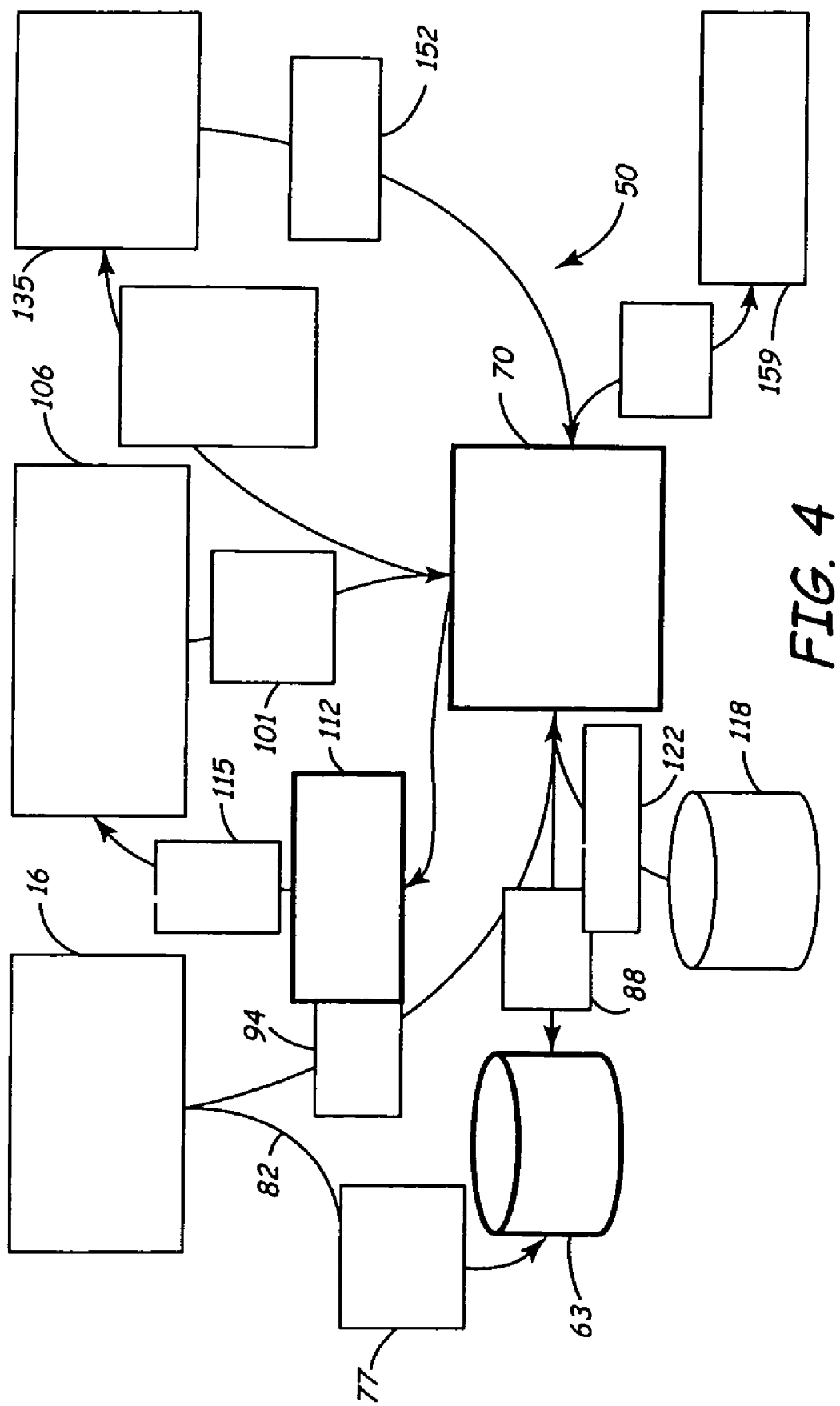
FIG. 4 is a schematic diagram of the system and data flow of the invention.

FIG. 4 illustrates a further aspect of the invention in which a second medical provider 135 receives either the automatic event notification service signal 112 or, preferably, another form of notification signal 144 which has been generated by another medical provider, such as first medical provider 106. Notification signal 144 is shown as a post-triage type of notification, i.e. after the initial analysis of the high relevance physiologic data has occurred by a first medical provider. The second medical provider may be a more specialized or more highly qualified provider, such as a cardiologist, surgeon or other type of physician. In one embodiment, notification signal may include recommendations or commentary from the first medical provider, and may be in the form of a secure asynchronous XML message, although various formats may be acceptable or preferred, including for example that necessary to enable the above described single page formatted communication. The notification signal 144 may also be formatted for display on a mobile or stationary device of medical provider 135, such as a handheld or other form of personal digital assist device. In this manner, even if the second medical provider is in the process of another activity, it may be possible to have the information observed or otherwise understood from the display and for the second medical provider 135 to direct appropriate medical care in the form of instructions to the patient and other care givers. In one embodiment it is contemplated for the second medical provider 135 to observe the emergent conditions of patient 16 and then dictate a secure voice message 152 (for example, a WAV file attachment or the like) for transmission back to a web-enabled site, such as web-site 70, for merger with the original data and automatic event notification service signal 112 for subsequent transmission to the patient 16. Of course, this information in the form of a combined signal of both the patient's physiologic data and the medical provider's interpretation and care recommendation may also be transmitted to a proxy or other patient advocate 159, as well as to automatic clinic appointment scheduler prompting mechanisms or the like.

Notification of patient 16 that a health-related message is waiting for review may also be sent to the patient advocate 159, such as a close relative of the patient, to ensure that the patient reviews, understands, and complies with the advice of the medical provider(s). This may be a sequence such as receipt of an electronic mail message urging activation of a link to the web-site 70 with automatic routing to message 152. In addition to the various communication options noted herein above, it is possible to have a dedicated channel, optional pop-up alert channel, webTV-like device, or dedicated internet service or portal available to the patient or patient advocate. This may be a service provided by existing or new communication service providers as a fee subscription or other revenue generating mechanism which is able to emerge and possibly block other communications until cleared by the recipient.

Figure 5:
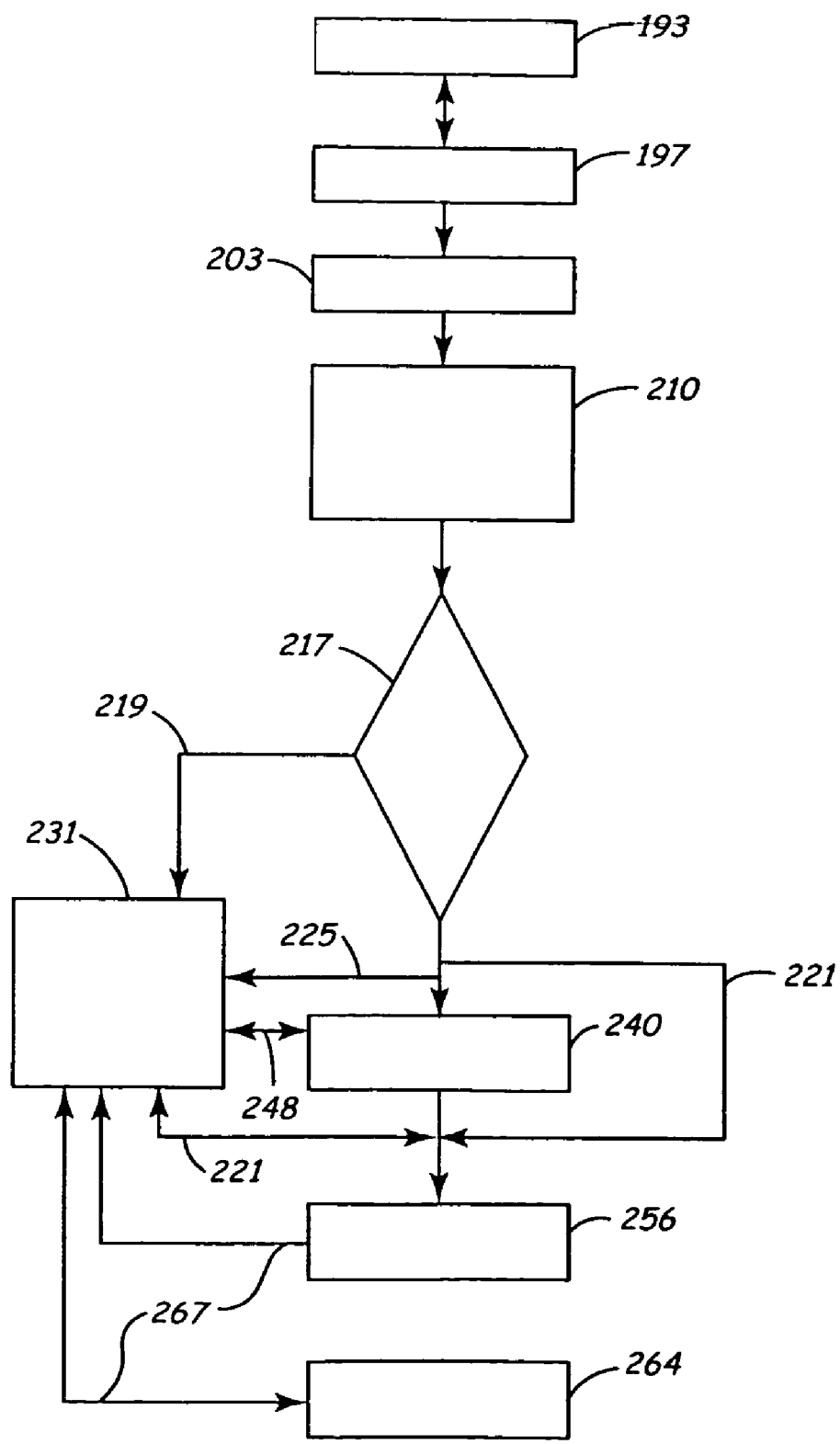
FIG. 5 is a decision making flow chart of the method of the invention.

FIG. 5 is a high level logic flow chart representative of one embodiment of the computer implemented steps of the invention and the flow of information. It is recognized that alternate flow paths may be implemented within the scope of this invention while still achieving the novelty, inventiveness, and technical contribution that the inventors are merited. Step 193 represents the detect and store features of the medical device that is monitoring the patient or user of the device. Step 197 represents the interrogate function to query and receive physiologic data from the medical device which is likely implanted within a patient. It is recognized that this function step may be obviated for a device which is external in view of different power management options. Step 203 represents the transmission of data to a remotely located patient management database 210 for storage and processing of the received physiologic data. Step 217 represents the analysis and set point computation steps necessary to determine whether the data received comprises particularly high relevance data that necessitates an alert. If an alert is not warranted then at step 219 the data is routed to a web site for instantaneous presentation upon authorized access by either the patient, a proxy or a healthcare professional. If an alert is warranted, then at step 221 a formatting process is implemented, and at step 225 a signal is sent to web-site 231 notification routine causing a non-secure alert signal 240 to be transmitted in a push fashion according to pre-set protocol to healthcare providers. These providers in turn query the web site by rapid return link activation 248 in either a secure or non-secure manner which permits transfer of content rich rendered and formatted signal 256 to the healthcare providers via the web site, and with the signal comprising the high relevance physiologic data necessary for rapid analysis and comment/action by the healthcare providers, leading to transfer to the patient and proxy 264 again via the web site at step 267 with such comment/action recommendations riding thereon.

Figure 6:
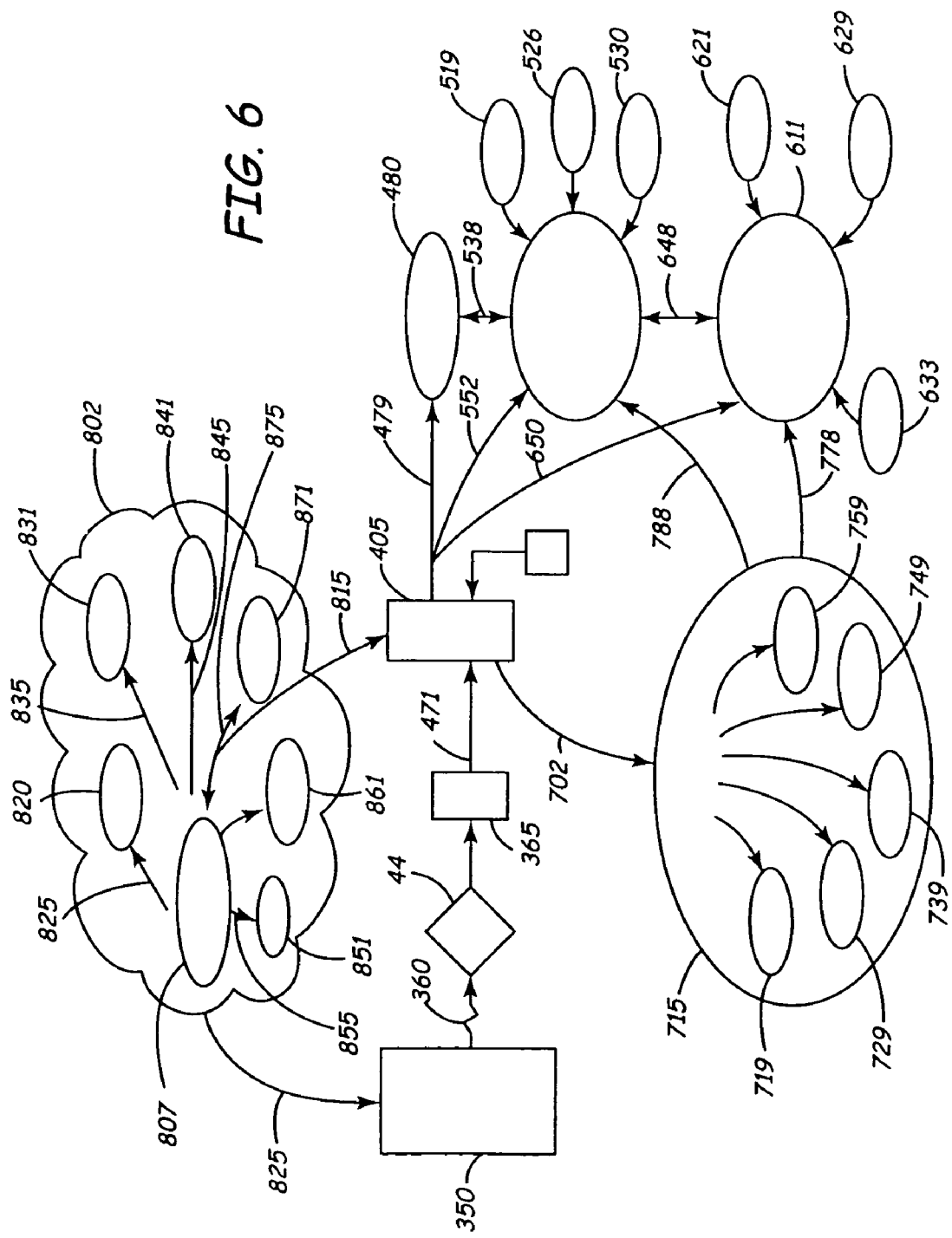
FIG. 6 is a schematic diagram of multiple embodiments of the invention.

FIG. 6 discloses another embodiment of the invention in which patient 350 is shown in a home setting and having one or more of an implanted medical device 14. These devices may include pacemakers, defibrillators, neurological devices, drug pumps, implantable monitors, or any other type of device which can act as a source of physiologic and medical device data that can be suitably transferred from the device out of the body. Where there exists a plurality of devices associated with one patient, the devices may also communicate between one another. The data communicated can be of several types. It may be data about the status of the device itself, such as battery status, programmable parameters, or device performance. It may be data which is sensed by the device such as electrical data or other data from specialized sensors. The transmitted data may also be processed or refined data such as prediction of an upcoming event.

Transmission 360 signifies transmission of data from the implanted device 14 to external remote monitoring instrument 44. This may be a single or a multi-step process. For example, in a single-step process, data is transmitted directly from the implanted device into a monitor which is connected to a communication system such as a telephone 365, which is only shown in representative rather than mandatory fashion. In a multi-step process, the implanted device transmits data to an intermediate device such as a transponder which then subsequently sends the data to a device connected to a communication system. Any portion of this system could either be hardwired or wireless. The wireless system could use any type of wireless technology, including but not limited to radio frequency or infrared communication. In addition, any portion of the system could also do additional data synthesis or processing either for compression, prediction, correlation, or any other reason for data analysis. In addition, the remote monitor could capture data from sources other than the implanted device such as other external instrumentation, or any other source of data in that environment, if desired. The connections to these other data sources could be either hardwired or wireless. The data could be combined in the remote monitor, processed, or transmitted separately.

It should be recognized that server 405 represents a networked computing system which may consist of additional hardware and software including databases, operating systems, communications channels, and all other necessary components required to receive large volumes of data from large numbers of users around the world and to be able to store, refine, analyze, and retransmit data. The communications network employed could be either private networks, virtual private networks, or public networks like the internet. It is to be understood that the server may also be connected to other computers on either private or public networks and the implanted device data could be aggregated or otherwise combined with other data or services in the server.

Accordingly one embodiment of the invention is a system or method of service or alternatively a business method by which is provided a system for automatic implementation of a chronic remote patient monitoring service. The service transmits high relevance data of a medical and physiologic type from a patient having at least one implanted and/or wearable device. The system to provide this service product 471 comprises a server 405 hosting medical and physiological data accessible via a remote monitor in data communications with the server. At least one medical device 14 is implanted in a patient 350 or wearably located on a patient being in data communication with the remote server, and the server is web-enabled to host and provide multi-directional data collections from various services including the patient. In one embodiment the at least one implanted and/or wearable medical device is in wireless communication with the remote monitor to enable data communications when the patient is ambulatory. The service provided also includes programmable parameters to bill the patient, or others, for the services provided.

FIG. 6 further illustrates data 479 flowing from server 405 to a physician 483 or other clinician such as a paraprofessional or nurse who wishes to view the implanted device data or any of the other aggregated data available on the server. As discussed herein above, the physician or other clinician would have a password (or other access control) which would grant access to the specific data, and access could be granted either by the patient or by other appropriate authentication authority. The data 479 could flow from server 405 to the physician through a variety of means, including private or public networks such as the Internet. To maintain security, the server is presumably protected by a variety of security mechanisms such as a firewall or other mechanisms which control access. If the data moves over a public network like the Internet, it is anticipated that the data would be encrypted. It is also anticipated that other services may be provided along with the data to the physician, such as scheduling services, updates in medical information, or any of a large variety of physician office services. In return for access to this high relevance data 479 and/or the services, it is possible that the physician or clinician or clinic employing the physician or clinician would pay a fee for the data or services. Any of a number of billing and collection mechanisms can be envisioned for this fee. The fee could be single use; that is, fee for each data view, or a fee for each service used. Alternatively, the fee could cover a given time period such as a monthly access charge or the like. The services could be versioned in multiple versions ranging in complexity and richness and correspondingly having different prices. The billing and collections process could be done in any number of ways, including direct computer-to-computer transaction, monthly statements, direct credit card transfer, or any other mechanism commonly used for business-to-business billing and collection transactions.

Accordingly, a valuable service is enabled by use of the inventive full-cycle information system by which the system is network-enabled to implement a chronic data management and monitoring service for remote patients and medical devices. The system includes: a server computer such as that shown and represented by server 405 which is configured for hosting data transmitted from the remote patients and medical devices; a client computer providing access to a plurality of users of the service such as, for example, clinician-based computer 483. In this manner, and with the stream of high relevance patient and service data available, the server computer provides a user interface whereby the plurality of users are authenticated prior to accessing the data, and the service is available via one of a secure web-based channels to enable an authenticated user to access data pertaining to a specific patient and/or medical service. Various billing and collection systems may be employed with this system, including, for example, services by which are utilized computer to computer transactions, monthly statements, direct credit or debit card/account transfers, micro-payment-systems and business-to-business systems. It may be possible for query-generated service revenue to be integrated as well, for example, responsive to various user inquiries as discussed herein.

FIG. 6 further demonstrates an information network 510 within a healthcare system. The healthcare system may be a clinic, a multi-specialty clinic, a hospital, a hospital system, or an integrated delivery network of multiple hospitals, clinics, and outpatient facilities. Healthcare system information network 510 typically collects data from multiple sites within the healthcare system such as, but not limited to, radiology results 519, clinical laboratory results 526, or pathology results 530. Typically, physicians or other clinicians working within the healthcare system have access to this information network as shown by arrow 538 between the physician 483 and the healthcare system information network 510. This highly interactive system is a valuable service product which enables implementation of high relevance physiologic data transfer and exchange. This alone as a real-time, virtual real-time, or "archived" retrieval service is a product of considerable importance and value, particularly when combined with the high relevance source data that is coming from the patient's device(s), and which may be further formatted or otherwise rendered as discussed herein.

Accordingly an internet based information network service for implementing medical data transfer and exchange in a health care system is provided. This service comprises means for collecting the medical data from multiple remote sites; and interference means for accessing said means for said collecting by authorized agents. Interface means includes controls for authenticating a user for the service and provides selection criteria and display at any one of said multiple remote sites for the user. It is anticipated that this service will provide substantial value to the users and is therefore subject to optional payment systems as disclosed herein elsewhere.

FIG. 6 shows a further example of this unique data flow system and methods of applying knowledge enhanced value to high relevance data. The figure further demonstrates data or other services flowing from server 405 to healthcare system information network 510. It is envisioned that healthcare systems will import data from the server to integrate with the other clinical data on that patient within their respective healthcare system information network 510. FIG. 6 shows arrow 552 between server 405 and healthcare system information network 510, signifying both a data/service path and a fee being charged for the healthcare system information network to have access to the data and services on the server. The data on the server represents important information about the status of patient 350 or of the device 14 and would be valuable to be integrated with other clinical data about the patient who is followed within that healthcare system. The healthcare system can provide either more effective or efficient care by having data available from the server. For example, it is less expensive for the healthcare system to check the status of an implanted device by having the data transferred from a patient's home than to have the patient come to the healthcare system and use a clinic appointment to have the data interrogated. The value that is created through this more efficient device follow up mechanism is one basis of such a fee. Alternatively, the data may indicate that the patient is deteriorating and it becomes less expensive to anticipate this deterioration and treat it while the patient is at home than to wait for the patient to get sicker and come into the healthcare system. Similarly, this additional value may become the basis for a fee. In either event, the healthcare system has an economic and performance incentive to pay a fee to have access to the high relevance data on the server. As in the case of the physician or clinician, any of a variety of billing and payment mechanisms can be envisioned. A fee could be charged for each time the server is accessed. That could be weekly, monthly or yearly access charges. There could be various versions of access differing in richness, depth, or quantity of information presented or transferred. There could be a variety of billing or collection mechanisms, including direct computer-to-computer transfer, billings statements, or any of a variety of other mechanisms.

Accordingly, a system for implementing computerized health care information services is provided. This system is a network capable of collecting medical data from various remote locations including a patient with a medical device. The information service comprises a server hosting medical and physiological data collected from a patient at a remote location, with the server being in data communications with a remote monitor that collects the data from the patient having at least one implanted and/or externally worn medical device. A physician's station is provided, and a health care system information network in data communications with the server and the physician's station is also provided. A billing service for the remote management of the patient's health, including a service of the performance of at least one implanted and/or externally worn medical devices, also provides communicating with the physician's station for expert opinion and advising the patient in real-time, and to advise as to proper procedures to follow for therapy and medical care.

FIG. 6 further shows a disease management organization 611 operating in association with a clinician 483 and a healthcare system 510. Disease management organizations typically undertake the responsibility of managing a patient's disease in its entirety and may be contacted using a variety of mechanisms such as yearly fees, risk sharing, or captivated/capitated payment. A disease management organization can either exist as part of a healthcare system or may be outsourced. Disease management organizations typically exist to manage patients with chronic diseases such as heart failure, diabetes, asthma, arthritis, and cancer, although any disease could possibly be managed by a disease management organization.

It is recognized that disease management organizations typically attempt to capture and synthesize a variety of types of information. The figure demonstrates information coming from clinical guidelines 621, data from point of care instrumentation 629, and data from patient interactions 633, but many types of information are used by disease management organizations to manage a patient that are in addition to those shown for example. Arrow 648 between the disease management organization 611 and the healthcare system information network 510 represents that the disease management organization may use data and services in the healthcare system information network 510 and may also source data and/or services to the healthcare system information network.

Once again, FIG. 6 also demonstrates how data and/or services may flow from the server 405 to the disease management organization 611. The data 650 flowing from a server 405 becomes another source of information which is used by the disease management organization to manage the patient or function more effectively as an organization. Similar to the case for the healthcare system, it is envisioned that the data and/or services that can be supplied by the server will allow the disease management organization to treat the patient either more efficiently or more effectively, saving money and improving care in either case. In return for the data, the disease management organization pays a fee to have access to the data/services. All of the comments about billing and payment mechanisms discussed in the healthcare system and clinician case also apply to the disease management organization. In addition, various payments structures can also be envisioned based on the way that the disease management organization contract is written, including subscription fees, risk sharing, or captivated/capitated fees.

What is provided, therefore, is a system for implementing a disease management service in which a remote chronic patient with an implantable medical device and/or wearable device(s) is provided. The service includes multiple users of data and information exchange systems cooperating to provide the service for continuously managing the chronic patient's disease in a highly efficient and value-added manner. In one embodiment, the system comprises: a server hosting medical and physiological data collected from the patient; a physician's station and data communications with the server; and a health care system information network being in a bi-directional communication with the physician's station and further having a data communication with the server; and a disease management organization in bi-directional communications with the health care system information network. The server includes at least one set of databases of information concerning the patient, so that the database is structured to assist the disease management organization in the management of the patient. In addition to the basic data, as discussed herein, particular formats and rendering of the data is also available for a fee based access in order to improve the utility of the high relevance data to the disease management organization.

FIG. 6 further shows data and/or services 702 flowing from server 405 to a medical device provider/manufacturer 715 (such as Assignee of the invention, Medtronic, Inc.) and/or medical product/service provider. It is envisioned that the data on the server could be used by medical device manufacturer 715 in a variety of valuable ways.

A first embodiment shows the data 702 flowing to a research and development department 719. It is anticipated that having access to large and highly relevant databases of patient physiology and device performance, will be a valuable source of information in the design of new devices.

A second embodiment shows the data 702 flowing to the product planning department 729. Knowing how devices are programmed, device longevity, and potential failure modes will be usefully in planning new features and new devices. This is information which is very valuable and available from data 702.

A third embodiment shows the data 702 flowing to the department responsible for post market surveillance 739. Many governmental entities, e.g., countries, require manufacturers to perform post-market surveillance on their medical devices to understand device performance and failure modes and mechanisms. Having this data available through the server 405 will allow more accurate, timely, and complete information capture; all of which is highly valuable. Indeed, for this and other uses, the particularly high volume of highly relevant data in a full cycle system distinguishes this invention from others.

A fourth embodiment illustrates the data 702 flowing to a sales and marketing department 749. The server data can help to evaluate whether the implanted device is appropriate for the patient's condition. For example, if the patient has an implanted ventricular defibrillator that does not have any atrial fibrillation therapy modalities, and the data demonstrates that the patient is having episodes of atrial fibrillation, the sales and marketing department could contact the physician to replace the implanted device with a different device that is more effective in treating all of the patients' conditions. This offers the opportunity for cross-selling or up-selling, particularly at the time of device replacement, and is a very good example of the knowledge enhanced value of data/services represented as data 702.

A fifth embodiment demonstrates the data 702 flowing to clinical databases 759. These clinical databases are envisioned to be large collections of data captured from patients who send data to the server and are maintained longitudinally over time. It is envisioned that these could be very large databases involving tens or hundreds of thousands of patients who are being followed for long durations, including possibly, years. These databases would offer information which is simply unmatched and unattainable in any other way involving device performance and patient physiology on very large numbers of patients over prolonged periods of time. Using any of a variety of data mining mechanisms, some of which may be known in the art, it is anticipated that new patterns and new knowledge can be gained through the analysis and synthesis of these novel databases. For example, it is anticipated that device performance, failure modes, and longevity will be able to be estimated and predicted with far better accuracy than is possible today. In addition, it is anticipated that evaluating patient physiology will allow patterns of disease and prediction of future disease, rate of onset, or disease progression which are not currently possible without this invention.

FIG. 6 also illustrates selling or sharing the results of this data mining from the clinical databases 759 (or other subgroups of entity 715) to a disease management organization 611, as shown by arrow 778. Disease management organizations need to understand disease progression and cost structures in order to be able to profitably run their business. Such organizations must estimate the costs that they will incur in taking care of patients when they contract with a healthcare system. Better information that allows more accurate prediction of costs is highly valuable to these organizations. In return for this better predictive information which is a result of the data mining of the high relevance clinical databases, the disease management organization pays a fee. This fee could be structured in any of a variety of ways. For example, the disease management organization may want data only on its own enrolled patients which are contained in the clinical database and would pay either a subscription or access fee to be able to estimate costs of their enrolled population. Alternatively, disease management organization 611 may be interested in population behavior that would allow it to better estimate future costs. In this case, the fee could take the form of intermittent updates, fees for algorithms, fees for analyst's reports, or any of a variety of data product or data-service related mechanisms. Any one of a number of billing and collection mechanisms could be utilized including direct computer-to-computer transfer, standard invoicing and payments, or any other mechanism for billing and collection.

In similar fashion to that above, data and/or data-products and/or data-services from the clinical database (or other subgroup of entity 715) flow to the healthcare system information network 510 via arrow 788. In similar ways as those described for disease management organizations, healthcare systems need to be able to predict and anticipate operating costs, utilization, quality, and other operating metrics. The information which is synthesized through the data mining of the large clinical databases can be a source of extremely valuable information to healthcare systems. For example, a healthcare system could compare device failure or malfunction rates within its healthcare system to population statistics to determine quality of device implantation and follow up. Alternatively, a healthcare system could compare the physiology or complications from its patients to population statistics. Healthcare systems could predict utilization of their services by evaluating complication rates within large populations of patients and extrapolating that data to their own population. Many other valuable types of information can be envisioned, and particularly when using high relevance and rapidly accessible high volume data/information which is nowhere else found. In return for this exceptionally unique information, the healthcare system would pay a fee to entity 715. These fees could be structured in a variety of ways depending on the type of information, frequency of interaction and depth of richness and utility of information. Potential mechanisms include time based subscriptions, single use access fees, and multiple versions. Invoicing, billing and payment could be carried out as well through a variety of mechanisms, including direct computer-to-computer transfer, credit card billing, paper invoicing and checks, or any of the multitude of ways of billing and collecting in business.

This example shows an information system for generating medical device performance data, in real-time, to enhance product performance and adapt business methods to provide a continuously improving service to a chronic patient. The information system comprises a server hosting data transmitted from a remote patient; a plurality of client computers providing access to the server; and a medical device related entity computer being in data communications with the server wherein device data is managed to provide at least a certain quantity of information derived from a sub-group of the medical device entity, for use by engineering personnel and others in disease management organizations or health care systems.

FIG. 6 further illustrates relationships and inventive methods of performing tasks and of doing business involving patients, consumers, and others using interrogated high relevance implanted device data on the internet or web-enabled system 802. This figure shows data being transferred from the server 405 to an internet website 807 which is a customized website, similar to that earlier described in relation to web-based site 70 of FIGS. 2-4. Site 807 is representative of a plurality of various sites which could be used in this application. This transfer could involve raw data or synthesized or refined data, and is represented by arrow 815. The transfer of this data could either occur continuously or intermittently depending on the application. The data, or refined, synthesized, or analyzed data/signals could either reside on the website 807 or the website could use the server as a source of data when queried by the user.

A user may access website 807 and view the data supplied by the server. This creates a complete loop of high relevance, fresh information starting with the patient (or other entity) interrogating the implanted device 14 with data flowing through the remote monitor, through a communications channel such as a telephone or other means, to a server 405 (or element functioning as such), to a website 807 and subsequently back to the patient, as shown via data/services arrow 825. This closed loop can serve as a system by which the patient changes something in this environment based on the information supplied by the interrogated device.

For example, the patient may change a dose of medicine, alter their lifestyle, or diet, or any other aspect of his/her medical care based on the updated information which is supplied through website 807. It is anticipated that this website will display the most recent data along with a longitudinal record of the patient's data in the past. In addition, the patient's individual data may be compared to population statistics which are available on the server which would allow the patient to compare his particular medical condition to larger numbers of patients with similar problems. It is also anticipated that the patient will interact with the website to supplement the data coming from the server with additional user-entered information such as current drug regimens, quality of life information, lifestyle information, or any other information which could be useful when stored on website 807 and aggregated with the implanted device data. This further information seeking may also serve as a rating mechanism for rating the relevance and value of the user's inquiries in relation to the observed physiologic condition. This rating may then be a factor in further actions, including fee related actions.

It is contemplated that the user (whether patient or another user) will pay a fee for the services available on website 807. This fee might typically take the form of a monthly subscription fee to allow the user to access the website and the personal data residing at that site. Any of the methods used to bill and collect payment on internet sites such as credit card billing or direct billing could be used. It is also contemplated to provide multiple versions of the service available, including basic versions which may be lower priced or even ranging through richer and deeper applications and service offerings which will be priced accordingly. The financial transactions may be done using encrypted data transmissions as is common on public computer network such as the Internet: The data transmission and medical information transmission can either be done using encryption or might also be done in a non-encrypted format.

It is also anticipated that the patient will be able to designate other users who can log on to the patient's account on website 807 to view the patient's specific data and information. These users might include family members, homecare givers, friends, advocates or any other person that the patient designates such as in a "friends and family" list. It is also anticipated that any one of the friends or family could also pay for the patient's account by billing a member of the "friends and family" list rather than the patient himself. In addition, it is possible that there would be access charges for the designated users which could range from single transaction fees through monthly subscription fees. Alternatively, charges might be adjusted according to health plan providers in view of the positive economic impact to a health care system when a patient and/or patient's friends or family are actively involved in the patient care or monitoring. It is also important to note that the hardware or software components of the system which are required in the closed loop could be bundled with the online service charges. For example, the remote interrogation device, might be purchased directly by any one of the potential users of the system, such as the patient, the physician, the healthcare system, the disease management organization, or a friend or family member. Alternatively, the cost of the remote monitor could be included as part of the internet service fee charged or accessed on website 807 in return for a subscription of minimum length such as two or three years. Additionally, software upgrades either to the remote monitor or the website could be purchased directly by any of the users of the system or also could be bundled within the overall Internet service offering. Again, although not envisioned as the primary way of charging for this service, it is possible that either the healthcare system, disease management organization, or other healthcare entity may elect to pay for the Internet service for the patient to ensure that the patient has this service that ultimately will be of benefit to that healthcare entity. As will be further discussed, website 807 is also connected to other health sites who may extract value by having patients have the customized website 807 service offering. It is conceivable as well that one or more of these other websites could pay the access fee for the patient to such a website 807.

FIG. 6 also shows links between website 807 and other Internet health sites. There are currently many health sites on the Internet with a variety of information, service, and revenue models. Most of these sites benefit by having additional users log onto their sites. Website 807 could structure business relationships with these health sites whereby users on would become aware of pertinent or relevant content on other health sites 820. If a user transfers from website 807 to that other health site, the other health site would pay a fee to website 807 for delivering a user to their site. This communication and fee structure is shown, for example, by arrow 825.

This figure also illustrates the connection between website 807 and the websites of pharmaceutical companies 831 on the internet. It is anticipated that website 807 may contract with pharmaceutical companies to make information about their products available to users of website 807. If a user moves to the website of a pharmaceutical company or uses the services of a pharmaceutical company, it is anticipated that company would pay a fee to the owner at website 807, indicated by data and revenue arrow 835. Several different fee structures can be envisioned. For delivering a patient to a pharmaceutical site, a "click through" fee could be generated. If the patient purchases additional services on the pharmaceutical site, a fee which could represent a percentage of revenue or an additional one time fee could also be generated. For example, if a user ends up getting a prescription for a drug through their interaction with the pharmaceutical site, the pharmaceutical company could pay a portion of that revenue back to website 807. In addition, if the patient becomes a user of other services which are offered by the pharmaceutical company such as enrollment in a disease management program, then a portion of related or attributable revenues would also be returned to website 807. Additionally, patient data could flow to the pharmaceutical company if permitted by the patient. The pharmaceutical company may have interest in evaluating patients responses to medications and the high relevance data collected by the implanted device and offered at website 807 may be valuable data to the pharmaceutical company. In this case, a fee would be charged to the pharmaceutical company for the data. This could either be one time access fees or fees for access to data over more prolonged periods of time.

Also demonstrated is a connection between website 807 and a clinical trial organization 841 such as a contract research organization. Clinical trial organizations typically perform clinical trials for manufacturers of pharmaceuticals or devices. There are a number of different ways that internet based interaction could occur. Website 807 could contract with a clinical trial organization to identify patients who may set the criteria for clinical trial enrollment. If a user of website 807 meets the enrollment criteria, website 807 could inform the patient that they could be eligible for a clinical trial and refer the patient to the clinical trial organization for enrollment. This could be done either by connecting them to the clinical trial organization website or through more traditional means such as a phone number or an office contact. The clinical trial organization would pay a fee for referring the perspective enrollee. If the patient actually enrolled in the clinical trial, one or more additional fee(s) could be generated. Another interaction is that data collected at website 807 could be useful in the monitoring and management of the clinical trial. In return for the clinical trial organization having access to patient data at website 807, which may make the clinical trial more effective, efficient, or faster, the clinical trial organization would pay a fee for data access. These fees and data-related products/services are represented by arrow 845.

FIG. 6 also shows the interaction between website 807 and various retailers 851 on the internet. These may be retailers offering medical equipment, but could also include retailers selling diverse items such as books, exercise equipment, or virtually any item which may be of interest to the user of website 807. The operator of website 807 would contract with various internet retailers to deliver patients to their sites based on their interests and/or ratings as well as the data which is acquired from the implanted device, all of which may be done automatically based on the patient's physiological data or other mechanisms. For example, if the data from the implanted device indicated that the patient was having episodes of a particular type of arrhythmia, the patient could be referred to a book retailer with specific books on that arrhythmia. Fees would be generated through a variety of mechanisms. The store would pay a fee for the referral of the patient to the store website. If the patient actually accesses and/or purchases items at that online store, a percentage of the revenue would flow back to website 807. These data services/products and fees are designated by arrow 855.

The figure further demonstrates the interactions between website 807 and other major internet companies 861 such as major portals, search engines, internet service providers, and the like. Many of these companies generate revenue based on advertising, which depends on user volume. Customized websites 807 could create arrangements with other internet companies to refer patients to those companies' websites if there is particularly relevant content or services available at those sites. For example, based on the implanted device data, a patient may be referred to a particular search engine which is particularly powerful in searching sites relating to that patient's particular problem. In return for the referral to the site, a fee is generated, as indicated by data services/products and fee arrow 865. In addition, if the patient subsequently purchases additional services from that site as a result of being routed to that site through website 807, a portion of review would be returned to website 807.

Similar relationships may be possible with patient advocacy groups 871, having valuable charters or missions which can have considerable tangible and intangible value to healthcare services, products, and decision makers. Such value may have a fee component, which is shown here as data services/products and fee arrow 875.

Accordingly, a system for implementing a network remote patient management services fee generating series of transactions comprises a server hosting patient management data for providing chronic monitoring of remote patients with chronic disease having implantable medical devices and/or wearable devices. The system further comprises a server being accessible via client computers wherein the client computers include a web-enabled system, a medical device entity website, a physician or other clinician site, a healthcare information network site, and a disease management organization. Each of the client computers are in data communications with the server to import specific data on which the patient management services billing schemes, for at least one service, are implemented.

Figure 7:
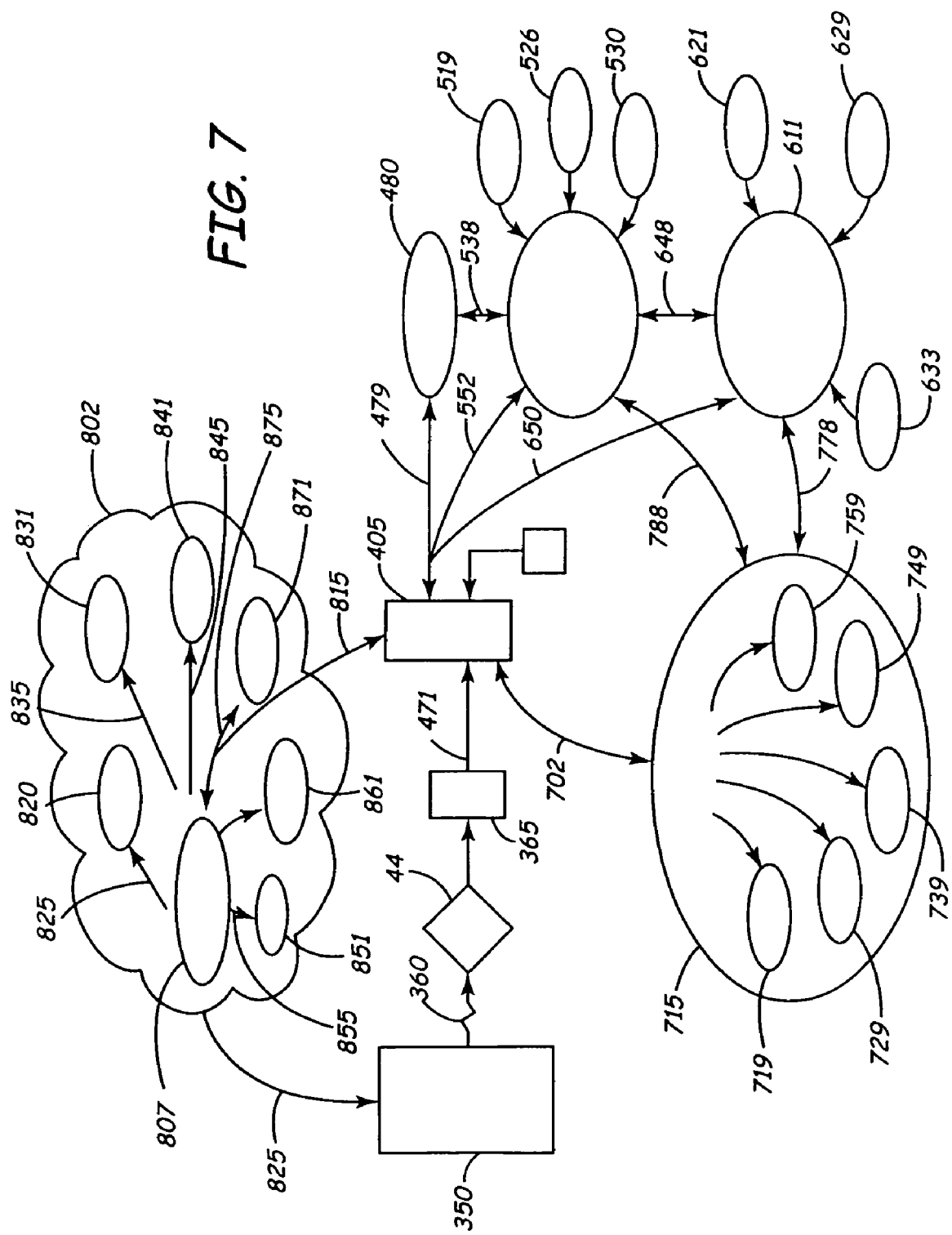
FIG. 7 is a schematic diagram of multiple embodiments of the invention.

FIG. 7 illustrates a variation of a method of providing data products and services, or alternatively methods of doing business, as described hereinabove. This variation places or positions the (patients' implanted device) server 405 at the center of the patient information flow. FIG. 6 shows, for example, most data flowing in one direction from server 405 to various users, which are now shown in FIG. 7 as bi-directional arrows.

This indicates that data could be flowing in both directions. The implanted data server 405, by being at the center of all of these information flows, could act as an aggregator of data and become the central repository of data about this particular patient. For example, while interrogated device data could flow from the server 405 to integrate what the healthcare systems information network 510 contains as other data on the patient, the data from the healthcare system information network 510 could flow back to the server 405. Similarly, rather than data flowing only from the server 405 to the disease management organization, data could also flow backward from the disease management organization to server 405. With multiple information flows coming to the server 405, it could become the central repository of multiple data sources. In return for this data access, the server 405 might generate payments to the sources of data such as the healthcare system information network or the disease management organization or alternatively process the returned data as a product/service after revision algorithms or updated databases for a further fee from the data providers. Therefore, in the same way that the information flow arrows are now two way, the revenue flow could also be bi-directional or optionally remain one-way. Of course, by having an aggregated set of the patient's data residing at the server, that data could then be repackaged with further knowledge enhanced value and resold to any of a variety of interested users beyond just the healthcare systems, disease management organizations, or integrated delivery systems, as may be agreed. Any of those organizations could also subsequently pay a fee for access to the integrated and aggregated data.

Accordingly, a personalized set of electronic web-based health and mobile health services may be provided and tailored to provide real-time and uninterrupted chronic patient management for remote patients with a medical device. These services include a billing scheme which is automatically implemented for services rendered, with the billing scheme comprising a server computer hosting the services accessible via client computers to a plurality of potential users of the service; and with the client computers being web-enabled to provide various service options to the user. The services are available over the internet to assist a specific user in locating and accessing a required service relating to the patient.

The above described invention relates to a patient-focused service of the highest order in which one or more implantable medical devices are implanted in a patient, and wherein the devices are adapted to connect the patients with caregivers for an uninterrupted management of chronic disease. Specifically, the invention also relates to a seamless flow of information between a surgical suite where the devices are implanted, the availability of support/expert systems, and improved availability of caregivers to the patient's home.

As noted, the health care systems worldwide need to provide better economic and lifestyle options for patients who suffer from chronic disease. Further, there is a need to empower patients to respond to their needs in a responsible way. Specifically, a system that enables patients and physicians to better treat chronic disease through the use of a remote monitoring communication and therapeutic technologies, is highly desired. More importantly, a total closed loop patient management system as well as support entity improvement tools which enable a continuous communication between patients, caregivers and physicians, will provide both patients and physicians with the knowledge that they need to make better treatment and organizational/resource management decisions.

Application of the invention(s) herein will move care beyond an episodic event to managing care over the course of one's disease. For example, a disease management system that allows physicians to select more appropriate treatment pathways in the management of chronic pain would require a bi-directional communication system between patients and remote physicians and caregivers. Specifically, as it relates to chronic disease, a system that enables patients and caregivers to have an uninterrupted continuous communication between them, would assist in the delivery of more effective and lower cost care for the patient.

The invention thus relates to multiple types of technologies integrated to support an infrastructure of networks for implanting a medical device, managing the medical device operations and performance, and chronic monitoring of patients while allowing them to lead a normal life at home and away from the hospital.

The invention exploits a combination of traditional medical technology with new advances in information and communication technology, coupled with the biologic sciences to transform the practice of medicine. More specifically, the invention creates services that will connect patients with their caregivers. This connectivity will allow connectivity to manage and especially enhance the flow of information between caregivers and patients, in order to provide the knowledge necessary to make informed decisions about the patient's health care over an extended period of time.

Figure 8:
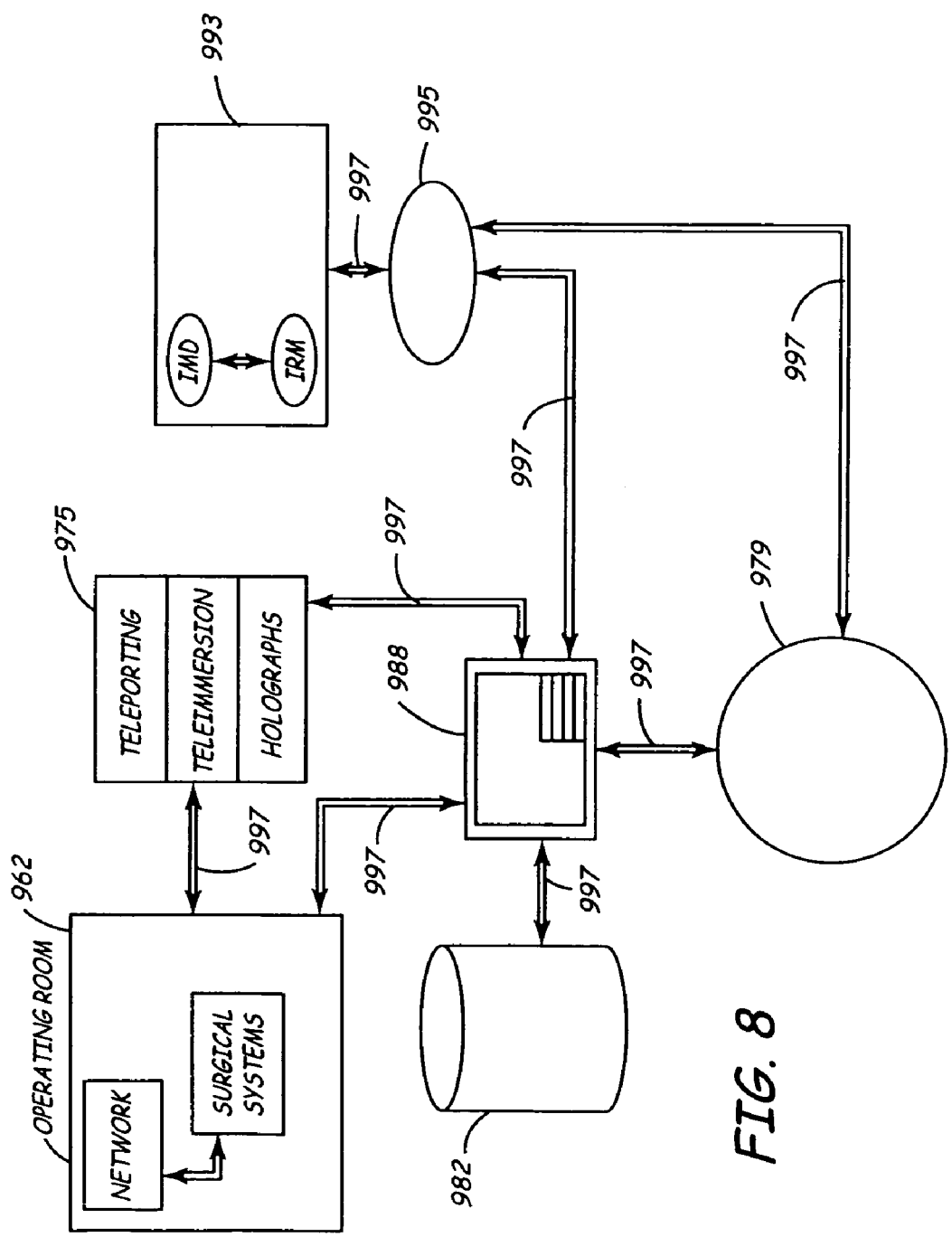
FIG. 8 is a schematic diagram of another embodiment of the invention applied to medical procedural facilities.

Another example of the integrated approach of the present invention is further illustrated as, optionally, starting in the Network Operating Room 962 (shown schematically in FIG. 8) where a clinical knowledge delivery system provides the physician with up-to-date information on the device to be implanted in the prospective patient. Specifically, the physician will be provided with complete care knowledge delivered in an environment that not only meets, but also anticipates, the surgical team's every requirement. The Network Operating Room 962 can, for example, bring a clinical specialist directly into the operating room through a virtual clinical support system.

It is anticipated that the specialist could be one who could offer in-depth product knowledge and has a deep understanding of a particular procedure so that technical service and support could be given at the exact moment in surgery when it is required by the physician. The network operating room also contains a high speed information portal 975, a conduit to deliver the patient's most relevant care information such as knowledge-enhanced radiographs, physiologic monitoring and information of anatomic and functional displays. All this, and similar functions, would be under the physician's control.

Video audio graphics, even highly realistic holographic imagery could be delivered where the physician needs it, when she needs it.

Further, an on-line consultation with physicians 979 remotely located from the operating room, could be initiated using, for example, an expert on-call program. As the on-call physician connects with the Network Operating Room, they are provided with a summary of the surgical plan and reference similar procedures using, for example, vast clinical data repositories 982 via server 988. Accordingly, the invention provides complete connectivity between all care providers whose instantaneous availability anywhere in the world to cover all aspects of care, is available in the operating/emergency/procedures room. Further, a parallel network of support systems 993 provides the patient in the home with connectivity to the primary care physician and other health care professionals via appropriate connectivity or communications interfaces 995. Thus the service is focused entirely on the patient, improving the physical condition and psychological outlook of patients, and reducing the anxiety among patients and others involved in healthcare.

The invention therefore provides a standards-based network for procedural room support, chronic disease management and medical device management services that are accessible to enable patients and physicians to effectively manage chronic disease through remote monitoring, communication, and data exchange on a continuous basis. The present invention provides virtual support systems to enable patients to lead a full life in spite of chronic disease, and appropriate revenue savings and fee generation results so as to encourage utilization of such a system. Connectivity may be via electronic, mobile lines 997 of data transfer, as disclosed in various embodiments herein.

This invention contemplates various systems and various types of methods to enable substantial economic and medical improvements to the business, art and science of healthcare. It is believed that these innovations and technical contributions provide a powerful combination of features and service advantages in view of the previously stated challenges to real-time effective management of certain classes of patient, such as those with chronic cardiac disease, constant infusion of medicines, neurologic stimulator requirements, or others, and that this has not been accomplished or realistically contemplated before by others.

What is claimed:

1. An internet-based method, comprising the steps of:
providing a networked computing system including a database network site, a patient medical services delivery application program, and a communications channel establishing a data and services delivery path;
a database network site receiving in a substantially continuous and real-time manner first data inputs uniquely representative of sensed physiologic information from a medical device configuration of a patient;
the networked computing system communicating with at least one web-enabled web-site and receiving web-site originated signals requesting access to first data inputs on the database network site and to services provided by the patient medical services delivery application program;
the database network site monitoring the data and service delivery path to determine a user's access to the first data inputs on the database network site and access to the patient medical services delivery application program, and
the database network site determining a revenue for the user's access to the networked computing system based upon at least one of the user's access to the first data inputs on the database network site and access to the patient medical services delivery application program.

2. The service method of claim 1 further including the step of providing said web-site and configuring said web-site with a user interface which includes a sign-in input to enable access to said database network site.

3. The service method of claim 1 in which the receiving step includes receiving at least one signal carrying information representing sensed physiologic status within the patient from at least one medical device located on or at least partially in the patient's body.

4. The service method of claim 1 in which the receiving step includes receiving signals carrying information representing actual physiologic phenomenon within the patient as sensed by at least one medical device located on or at least partially in the patient's body.

5. The service method of claim 1 in which the receiving step includes receiving signals carrying information representing actual physiologic phenomenon within the patient as sensed by a plurality of medical devices located on or at least partially in the patient's body.

6. The service method of claim 1 in which the networked computing system communicating and receiving step comprises providing a secure sign-in and validating an originator's security-related action prior to allowing access of the originator to the database information.

7. The service method of claim 1 in which the first data inputs provides intermediate information to enable further production of data representations enabling subsequent actions.

8. An internet-based method for a paid service to maintain connection of a remote implantable medical device configured patient to a database network and for medical device data exchange and processing comprising the steps of:
providing a web-site in a web-enabled system, the web-site having a user interface which includes a sign-in input to enable access to a database network site associated with said web-enabled system;
the database network site receiving in a substantially continuous and real-time manner first data inputs uniquely representative of sensed physiologic information from a specific implanted medical device configuration of a patient using said implantable medical device configuration;
the web-site receiving second data inputs requesting access to representations of said first data inputs available at said database;
the database network site enabling the originator of said second data inputs to have access to the database via the secure web site to view representations of said first data inputs; and
the database network site determining revenue for user access to said first data inputs.

9. The service method of claim 8 in which the enabling step comprises providing a secure sign-in and validating an originator's security-related action prior to allowing access of the originator to the database information.

10. The service method of claim 8 in which the first data inputs provides intermediate information to enable further production of data representations enabling subsequent actions.

11. An internet-based method for a paid service to maintain data connectivity of a remote implantable medical device-configured patient to a database network and to enable rapid medical device data exchange and processing of certain conditions, comprising the steps of:

a database network site receiving in a substantially continuous and real-time manner first data inputs uniquely representative of sensed physiologic information from a specific implanted medical device configuration of a patient using said implantable medical device configuration; and the database network site communication with at least one web-enabled web site to automatically deliver substantially real-time representations of said first data inputs from said database when certain conditions are met.

12. The service method of claim 11 in which the step of communicating includes initiating automatic software analysis of the first data inputs to determine whether any sensed physiologic activity is abnormal.

13. The service method of claim 11 in which the step of communicating includes initiating automatic software analysis of the first data inputs to determine actual values for any sensed physiologic activity.

14. The service method of claim 11 in which the step of communicating includes initiating automatic software analysis of the first data inputs to determine whether any sensed physiologic activity is indicative of a demonstrable or likely pattern of physiological activity.

15. A computer implemented method for improved data management in the healthcare industry by increasing patient engagement with recommended healthcare delivery modalities, comprising the steps of:
  a. providing an implanted medical device configured for automatic sensing of high relevance biologic data of the patient and wirelessly transmitting that data, or portions thereof, to an information parser of a healthcare professional;
  b. configuring a patient accessible electronic interface to receive signals representative of sensed high relevance biological data of the patient;
  c. providing from a networked computing system selectively programmable computer implemented rapid interpretations of the sensed high relevance biologic data and, when indicated, electronically sharing with the healthcare professional the details of the sensed high relevance biological data without resort to personal contact or face to face meeting between the healthcare professional and the patient; and
  d. providing information flow paths through a web-based site for the healthcare professional to further contribute to the knowledge database and patient engagement by offering the patient and a patient's designated advocate direct information about the high relevance biologic data thereby actively engaging the patient in a highly content rich yet efficient manner.

16. A computer implemented internet-based method for an improved connect and monitoring service to rapidly connect remote persons having implantable medical devices to a database network for medical device data exchange and analysis, said method being characterized in that it comprises the steps of:
  providing a web site having a user interface wherein the user interface includes a secure sign-in input to access a database network site;
  the web site receiving automatic inputs associated with a specific implanted medical device and user of the device;
  the database network site automatically confirming the identity of the implanted medical device and the user;
  the database network site enabling the user to access the database via the web-site to use the service for real time monitoring of high relevance physiologic data mined from all monitored data of the user; and
  the database network site communicating with at least one web-enabled web site and receiving web site originated signals requesting access to the database.

17. The method of claim 16 wherein said web-site further includes a proxy right access scheme to provide privileged access to a user's data by friends or family as programmed.

18. A computer implemented patient management network configured for automatically determining which connection protocols to follow to rapidly connect one or more remote persons having implanted medical devices to a database network for medical device data exchange and analysis, said network being characterized in that it comprises:
  a web site having a user interface wherein the user interface includes a secure sign-in input protocol to access a database network site;
  said web site providing for acceptance of automatic inputs to the web site associated with a specific implanted medical device and user of the device;
  processing routines and module for automatically confirming the identity of the implanted medical device and the user; processing routines and module for performing computer implemented analyses to determine which user groups to rapidly and selectively automatically access the database via the web-site for receipt of high relevance physiologic data mined from all monitored data of the user; and
  means for enabling the database network site to communicate with at least one web-enabled web site and to receive web site originated signals requesting access to the database.

19. A system for implementing a disease management service for a remote chronic patient with an implantable medical device wherein the service includes multi-users of data and information exchange systems cooperating to provide the service for continuously managing the chronic patient's disease, health care and medical devices comprising:
  a server hosting medical and physiological data collected from the implanted medical device of the patient;
  a physician station in data communications with the server;
  a health care system information network being in a bi-directional communication with the physician station and further having a data communication with the server;
  a disease management organization in bi-directional communications with said health care system information network;
  said server including at least one set of database of information concerning the patient wherein the database is structured to assist the disease management organization to manage the patient;
  means for monitoring access to the database and determining a fee based upon access to the database in the course of managing the patient; and
  said server including means for enabling the database to communicate with at least one web-enabled web site and to receive web site originated signals requesting access to the database.

* * * * *